(12) United States Patent
Martínez et al.

(10) Patent No.: US 8,124,331 B2
(45) Date of Patent: Feb. 28, 2012

(54) IN VITRO METHOD TO DETECT BLADDER TRANSITIONAL CELL CARCINOMA

(75) Inventors: Antonio Martínez Martínez, Vizcaya (ES); Laureano Simón Buela, Vizcaya (ES); Simon Santa Cruz, Vizcaya (ES); María Pilar Sáenz Jiménez, Vizcaya (ES); Corina Junquera Sánchez-Vallejo, Vizcaya (ES); José Javier Gómez Román, Santander (ES); Jorge Cuevas González, Santander (ES); Miguel Molina Vila, Barcelona (ES)

(73) Assignee: Progenika Biopharma, S.A., Vizcaya (ES)

( * ) Notice: Subject to any disclaimer, the term of this patent is extended or adjusted under 35 U.S.C. 154(b) by 903 days.

(21) Appl. No.: 10/550,608

(22) PCT Filed: Mar. 25, 2004
(Under 37 CFR 1.47)

(86) PCT No.: PCT/EP2004/003219
§ 371 (c)(1),
(2), (4) Date: Dec. 14, 2006

(87) PCT Pub. No.: WO2004/085676
PCT Pub. Date: Oct. 7, 2004

(65) Prior Publication Data
US 2007/0092878 A1    Apr. 26, 2007

(30) Foreign Application Priority Data
Mar. 26, 2003 (ES) .................................. 200300708

(51) Int. Cl.
*C12Q 1/00* (2006.01)
*G01N 33/53* (2006.01)
(52) U.S. Cl. ............................................ 435/4; 435/7.1
(58) Field of Classification Search .................. None
See application file for complete search history.

(56) References Cited

U.S. PATENT DOCUMENTS
2003/0087854 A1 * 5/2003 Monia et al. .................... 514/44

FOREIGN PATENT DOCUMENTS
WO    WO 00/68424    11/2000
WO    WO 02/102854    12/2002

OTHER PUBLICATIONS

Matsumoto et al. (Oncol Rep. Nov. 2004;12(5):967-71, Retrieved from the Internet <URL:http://www.ncbi.nlm.nih.gov/pubmed/15492779?ordinalpos=85&itool=EntrezSystem2.PEntrez.Pubmed.Pubmed_ResultsPanel.Pubmed_DefaultReportPanel.Pubmed_RVDocSum> on Oct. 5, 2009).*
Sturla et al. (FGFR3IIIS: a novel soluble FGFR3 spliced variant that modulates growth is frequently expressed in tumour cells, British Journal of Cancer (2003) 89, pp. 1276-1284, published online on Sep. 30, 2003).*
Capellan, D., et al., Frequent Activating Mutations of FGFR3 in Human Bladder and Cervix Carcinomas, Nature Genetics, vol. 23, Sep. 1999.
Chesi, M., et al., Frequent Translocation t(4;14)(p16.3;q32.3) in Multiple Myeloma is Associated with Increased Expression and Activating Mutations of Fibrolast Growth Factor Receptor 3, Nature Genetics, vol. 15, Jul. 1997.
Gygi et al., Correlation between Protein and mRNA Abundance in Yeast. Molecular and Cellular Biology, Mar. 1999, vol. 19 No. 3 p. 1720-1730.

* cited by examiner

*Primary Examiner* — Manjunath Rao
*Assistant Examiner* — Jae W Lee
(74) *Attorney, Agent, or Firm* — Kramer & Amado, P.C.

(57) ABSTRACT

The present invention refers to an in vitro method to detect a bladder transitional cell carcinoma, in an individual, to determine the stage or severity of this cancer in an individual or to monitor the effect of therapy administered to an individual with this cancer; to screen for, identify, develop and evaluate the efficacy of therapeutic compounds against this cancer in order to develop new medicinal products, and also agents that inhibit the expression and/or activity of the FGFR3 protein and/or the effects of this expression.

20 Claims, 5 Drawing Sheets

IN VITRO METHOD TO DETECT BLADDER TRANSITIONAL CELL CARCINOMA

REFERENCE TO SEQUENCE LISTING

The present invention includes a Sequence Listing submitted on compact disc, the contents of which are incorporated by reference in their entirety.

FIELD OF THE INVENTION

The present invention refers to an in vitro method to detect the presence of a transitional cell carcinoma of the bladder in an individual, to determine the stage or severity of this cancer in the individual, or to monitor the effect of therapy administered to an individual with the said cancer; to screen for, identify, develop and evaluate the efficacy of therapeutic compounds for this cancer in an attempt to develop new medicinal products and to agents that inhibit expression and/or the activity of the FGFR3 protein.

BACKGROUND OF THE INVENTION

Despite all the advances that have been achieved during the last 20 years, cancer is still one of the leading causes of mortality worldwide. Transitional cell bladder cancer is the most common cancer of the urinary tract; it is also the fourth most common cancer in men and the eight most common in women. Based on data from the International Agency for the Investigation of Cancer, GLOBOCAN, for the year 2000, more than 136.000 new cases per year are diagnosed in Europe, 13.000 in Japan and 56.000 in North America. More than 3-4 times this number of patients are treated and monitored at hospitals every year; and more than 49.000, 4.500 and 12.000 deaths are due to bladder cancer every year in Europe, Japan and North America, respectively (according to the International Agency for Research on Cancer GLOBOCAN 2000).

Transitional cell carcinoma (TCC) is the most common type of bladder cancer, accounting for more than 90% of all cases. The remaining cases are squamous cell carcinomas (7%), adenocarcinomas (2%), and undifferentiated carcinomas (1%).

Tumour grade and stage are the best prognostic indicators of transitional cell carcinoma of the bladder. Bladder tumours are graded cytomorphologically from G1 to G3 in decreasing state of differentiation and increasing aggressiveness of the disease according to the World Health Organization (WHO). With respect to stage or invasivity, TCCs of the bladder are classified as superficial papillary (Ta and T1), muscle invasive (T2 to T4), or the uncommon carcinoma in situ or tumour in situ (TIS).

Low-grade (G1) tumours are usually confined to the mucosa or infiltrate superficial layers (stage Ta and T1). Most high-grade tumours are detected at least at T1 stage (invading lamina propria). Approximately 75% of the diagnosed bladder cancer cases are superficial. The remaining 25% are muscle invasive at the moment of diagnosis.

The clinical importance of distinguishing superficial and invasive tumours stems from the need to perform radical cystectomy, with lymphadenectomy and bladder reconstruction in case of extended cancers (beyond the muscular layer). Tumours diagnosed in stages Ta and T1 allow the organ to be preserved and can be treated by transurethral resection and in some cases chemotherapy or intravesicular immunotherapy.

Patients with superficial TCC have a good prognosis but have a 70% risk of recurrence; these patients have to be monitored for tumour recurrence after treatment, following different protocols depending on the hospital, although the most frequent method is evaluation by the urologist every 3 months during the first 2 years, every 6 months for the following 2 years and every year thereafter. In spite of the high risk of recurrence, Ta tumours tend to be low grade and only 10-15% will progress to muscle invasion in 2 years; the percentage of T1 tumours that progresses to T2 stage is higher (30-50%).

Patients with invasive TCC have a poor prognosis; 50% of these patients at stage T2 or higher develop distant metastases within two years of diagnosis, and 69% of them die within 5 years. New diagnosis systems for early detection are needed given that 80-90% of patients with T2 or higher are first diagnosed at this highly aggressive stage and not in previous stages (de Vere White, R. W. and Stapp, E., Oncology, 1998, 12:1717-1723).

Currently, the best diagnostic system for bladder cancer in individuals presenting symptoms such as hematuria or dysuria, in the absence of infection, is cytoscopy. Based on statistical data of incidence and recurrence, it has been estimated that more than 500.000 cystoscopies are performed annually in the USA (van Rhijn, B. W. G., et al., Cancer Res., 2001, 61:1265-1268). Flexible cytoscopes are used to make the technique less aggressive, but it remains invasive and highly unpleasant, and it also requires some form of anaesthesia.

The prevailing non-invasive technique for diagnosis of transitional cell bladder cancer is to identify neoplastic cells by morphological examination of the cells in urine (Loh, C. S., et al., Br. J. Urol., 1996, 77:655-658). Cytology is currently used to follow up patients diagnosed with and treated for bladder cancer. On the other hand urine cytology can detect tumours in situ that are not detectable by cytoscopy as well as tumours located in the upper end of the bladder or the upper urinary tract, i.e. ureter, pelvis and renal, that are not easily accessible by endoscopy (Lotan, Y. and Roehrborn, J. Urol., 2002, 167:75-79).

Nevertheless several studies have shown that cytology has a very low sensitivity for bladder cancer diagnosis, missing up to 50% of tumours (Boman, H., et al., J. Urol., 2002, 167:80-83); in reality, there is no non-invasive method available to diagnose bladder cancer with high sensitivity and specificity (Boman, H., et al., J. Urol., 2002, 167:80-83). Such non-invasive methods would allow routine screening procedures for early detection of any transitional carcinoma including of the upper urinary tract, both de novo or in evaluating recurrence after treatment, including the detection of incipient invasive tumours or those at a high risk of developing aggressive disease.

Alteration of gene expression levels is tightly associated to uncontrolled cell growth and de-differentiation, common features of all cancers. The expression levels of the so-called "tumour suppressor genes", which act to block malignant cell growth, are repressed in tumour cells; and expression levels of the so-called "oncogenes", which act to induce malignant growth, are elevated in tumour cells.

Many of these genes have been associated to bladder cancer development, including Rb, p53, p16, p14ARF, cyclin D1 (Fujimoto, K., et al., Cancer Res., 1998, 52:1393-1398; Grossman, B. H., et al., Clin. Cancer Res., 1998, 8:829-834; Balazs, M., et al., Genes Chromosomes Cancer, 1997, 19:84-89). The alteration in the expression of these genes could be used as a diagnostic marker of transitional cell carcinoma of the bladder; among these proposed markers have been proposed nuclear matrix protein NMP22 (Soloway, M. S., et al., J. Urol., 1996, 156:363-367; Casella, R., et al., J. Urol, 2000, 164:1926-1928), Hyaluronic Acid and Hyaluronidase (Pham, H. T., et al., Cancer Res., 1997, 57:778-783; Hautmann, S. H., et al., J. Urol., 2001, 165:2068-2074), Basement Membrane Complexes (BTA) (Pode, D., et al., J. Urol., 1999, 161:443-446; Thomas, L., et al., Clin. Chem, 1999, 45:472-477, Carcinoembryonic antigen (CEA) (Halim, A. B., et al., Int. J. Biol. Markers, 1992; 7:234-239), Uroplakin II (Wu, X. R., et al., Cancer Res., 1998; 58:1291-1297), Scatter Factor/Hepatocyte Growth Factor (SF/HGF) (Gohji, K., et al., J. Clin. Oncol., 2000; 18:2963-2971), proteins of the keratin/cytokeratin family like cytokeratin 20 (Buchumensky, V., et al., J. Urol., 1998, 160:1971-1974), and cytokeratin 18 (Sánchez-Carbayo, M., et al., Clin. Cancer Res., 2000, 6:3585-3594), Mammary tumour 8-Ka Protein (MAT-8) (Morrison, B. W., et al., J. Biol. Chem., 1995, 270:2176-2182), Telomerase However, it is likely that many of the genes involved in the initiation and progression of bladder cancer are currently unknown. No marker to predict the prognosis and extent of bladder cancer has been proven useful in clinical trials (Miyake et al., 2002). (Miyake, H., et al., J. Urol., 2002; 167:1282-1287). The identification of differentially expressed genes in bladder cell carcinoma could lead to the identification of biological markers, which could be of significant value for the diagnosis, prognosis and treatment of this disease.

Once transitional cell carcinoma of the bladder has been diagnosed, transurethral resection is carried out to treat superficial papillary tumours; superficial TIS and T1 are treated, in addition to transurethral resection, with intravesicular treatment with *Bacillus*-Calmette Guerin (BCG). If the cancer is muscle invasive, the patient is treated by radical cystectomy; if the patient will not tolerate this surgery, radiation therapy or chemotherapy is used. The 69% percent of the patients with muscle invasive TCC die within five years after diagnosis, even after receiving treatment. Alternative therapeutic approaches are necessary to treat muscle invasive TCC with a higher efficiency; also needed are alternative therapeutic approaches to treat low-grade tumours more efficiently than through surgery, or to complement surgery in order to avoid recurrences and progression of the tumour to an invasive state.

Fibroblast growth factors (FGF) are a family of more than twenty proteins involved in the regulation of biological processes including cell proliferation, cell differentiation, cell growth, cell migration, morphogenesis, angiogenesis and tissue remodelling. The FGFs bind with high affinity to cell surface receptors (Fibroblast Growth Factor Receptors, or FGFRs) that have tyrosine kinase activity. The protein kinases are a family of proteins, which effect the phosphorylation of other proteins and play a key role in the regulation of many cellular processes (Hanks, et al., Science 1988, 241, 42-52). When the FGF ligand binds to FGFR, the FGFR is converted to a dimeric active form that autophosphorylates in the kinase domain; then the activated FGFR binds and phosphorylates other effector proteins, thus starting a signal transduction pathway from the cell surface to the nucleus (Crews and Erikson. Cell. 1993. 74:215-217). The loss of regulation of growth factor signalling pathways is a frequent occurrence in cancer.

Four FGFRs have been identified to date: FGFR1 (also called Flg, fms-like gene, flt-2, bFGFR, N-bFGFR or Cek1), FGFR2 (also called Bek-Bacterial Expressed Kinase-, KGFR, Ksam, Ksaml and Cek3), FGFR3 (also called Cek2) and FGFR4. All mature FGFRs share a common structure consisting of an amino terminal signal peptide, three extracellular immunoglobulin-like domains (Ig domain I, Ig domain II, Ig domain III), with an acidic region between Ig domains I and II (the "acidic box" domain), a transmembrane domain, and intracellular kinase domains (Ullrich and Schlessinger, Cell 61:203, 1990; Johnson and Williams (1992) Adv. Cancer Res. 60:1-41). The distinct FGFR isoforms have different binding affinities for the different FGF ligands, thus FGF8 (androgen-induced growth factor) and FGF9 (glial activating factor) appear to have increased selectivity for FGFR3 (Chellaiah et al. J Biol Chem 1994; 269: 11620).

Specific point mutations in FGFR3, that lead to the activation of its tyrosine kinase activity, have been previously associated to different syndromes related to bone development (Chen, H., et al. J. Clin. Invest., 1999, 104(11):1517-1525). Mutations in FGFR3 have also been detected in multiple myelomas (10-25% of tumours. Plowright et al. Blood 2000 Feb. 1; 95(3):992-8; Chesi et al. Blood 2001 Feb. 1; 97(3): 729-36; Soverini et al. Haematologica 2002 October; 87(10): 1036-40; Pollett et al. Blood 2002 Nov. 15; 100(10):3819-3821), in cervical carcinomas (3.5-25% of tumours. Sibley et al. Oncogene 2001 Jul. 19; 20(32):4416-8; Dai et al. Anal Cell Pathol 2001; 23(2):45-9) and in bladder carcinomas (Cappellen et al. Nat Genet 1999 September; 23(1):18-20; Sibley et al. Oncogene 2001 Feb. 8; 20(6):686-91; Sibley et al. Oncogene 2001 Jul. 19; 20(32):4416-8; Billerey et al. Am J Pathol. 2001 June; 158(6):1955-9) Activating FGFR3 mutations were detected in 40-50% of bladder tumours; the incidence was significantly higher, up to 80%, in low grade or superficial tumours than in high grade or invasive tumours; and the bladder cancer recurrence rates were clearly lower for tumours with a mutant FGFR3 (Kimura et al. Cancer 2001 Nov. 15; 92(10):2555-61; van Rhijn et al. Cancer Res 2001 Feb. 15; 61(4):1265-8).

Unexpectedly, the authors of the present invention have discovered, after thorough research and using different techniques, that the expression level of the FGFR3 gene and concentration of the protein is elevated in biopsies of bladder transitional cell carcinomas when compared with expression in normal bladder tissue and, moreover, the treatment of bladder cancer cell lines expressing high concentrations of FGFR3 with antibody against FGFR3 protein produce inhibition of cell proliferation of bladder cancer cell lines.

The authors of the present invention have also surprisingly discovered that the elevated levels of FGFR3 protein expression are predominantly associated with superficial tumours.

The present invention, therefore, provides a highly sensitive in vitro method to detect the presence of a bladder carcinoma, to determine the stage or severity of this cancer in an individual or to monitor the effect of therapy administered to an individual with the said cancer. Also, the present invention provides targets or tools for the screening, identification, development and evaluation of the efficacy of therapeutic compounds for the treatment of cancer of the bladder, particularly for tumour treatment, as neoadjuvant before resection or as adjuvant after resection with the aim of reducing recurrence and progression. Finally, the invention provides agents characterised by the fact that they inhibit expression and/or activity of the FGFR3 protein for the treatment of cancer of the bladder.

SUMMARY OF THE INVENTION

A first aspect of the present invention is to develop an in vitro method to detect the presence of cancer of the bladder, to determine the stage or severity of this cancer in the individual or to monitor the effect of the therapy administered to an individual with this cancer.

A second aspect of the present invention is an in vitro method to screen for, identify, develop and evaluate the efficacy of compounds to treat bladder transitional cell carcinoma.

An additional aspect of the invention lies in the use of sequences derived from the FGFR3 gene to establish the diagnosis and prognosis in vitro of bladder transitional cell carcinoma, and to screen for, identify, develop and evaluate the efficacy of compounds for the treatment of this cancer.

A further aspect of the invention consists in the provision of agents that inhibit the expression and/or activity of the FGFR3 protein.

Another aspect of the invention consists of a pharmaceutical composition comprising a therapeutically effective amount of at least one agent that inhibits the expression and/or activity of the FGFR3 protein together with at least one pharmaceutically acceptable excipient.

A final aspect of the present invention consists in a kit for carrying out the present invention.

DETAILED DESCRIPTION OF THE INVENTION

Figure 1:
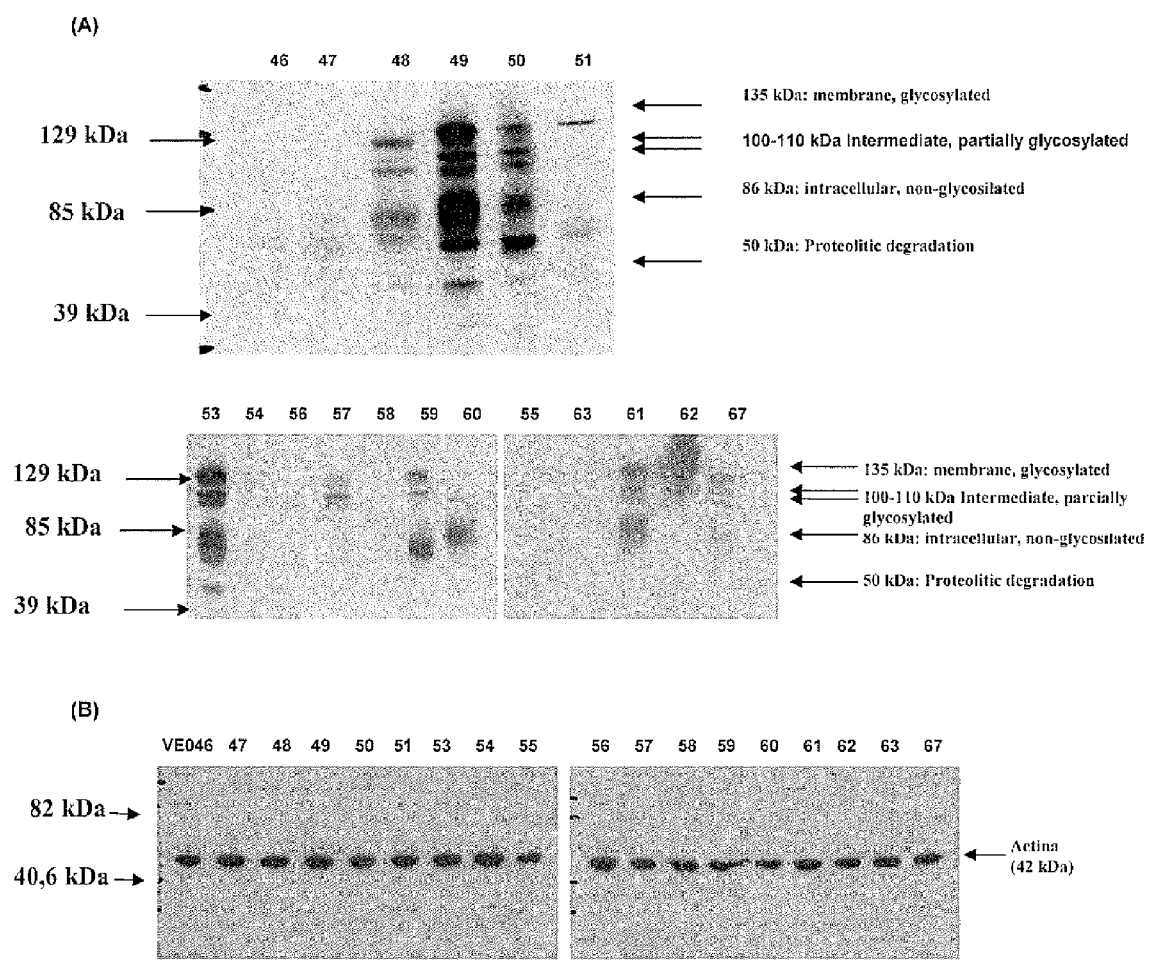
FIG. 1 shows results of Western Blot analysis of FGFR3 expression in samples of human bladder. Samples analysed were: Non neoplastic urinary bladder samples: 46, 55 y 63); Low grade superficial transitional cell carcinoma (G1, Ta) samples: 48, 49, 50, 53, 56 and 59; High grade lamina propria infiltrating carcinomas (G3, T1) (samples 57, 61 and 67), High grade muscle infiltrating carcinomas (G3, T2) (samples 47, 51, 58 and 60) and two samples of unknown stage (samples 54 and 62). In all cases 20 micrograms of total protein were loaded. Membranes were incubated with Anti-FGFR3 antibody (A) or Anti-actin antibody (B). The analysis showed various immunoreactive bands of different sizes: glycosylated form (135 kDa), the intracellular non-glycosylated form (85 kDa) and several intermediate bands (110-110 kDa) that correspond with different FGFR3 glycosylation states. Smaller immunoreactive bands (50 kDa) were also detected that may have result from proteolytic processing.

To facilitate the comprehension of the present patent application we give the meanings of some terms and expressions in the context of the invention:

The terms "subject" or "individual" refers to all species of animals classified as mammals and includes, but is not restricted to, domestic and farm animals, primates and humans. The subject is preferably a male or female human of any age or race The term "cancer" refers to the disease that is typically characterised by abnormal or unregulated cell growth, capable of invading adjacent tissues and spreading to distant organs.

The term "carcinoma" refers to the tissue resulting from abnormal or unregulated cell growth.

The term "bladder transitional cell carcinoma" refers to any malign proliferative disorder in bladder epithelial cells.

The term "tumour" refers to any abnormal mass of tissue generated by a neoplastic process, whether this is benign (non cancerous) or malignant (cancerous).

The term "gene" refers to a region of a molecular chain of deoxyribonucleotides that encodes a protein and may represent a portion of a coding sequence or a complete coding sequence.

The term "DNA" refers to deoxyribonucleic acid. A DNA sequence is a sequence of deoxyribonucleotides.

The term "cDNA" refers to a nucleotide sequence complementary to a sequence of mRNA.

The term "RNA" refers to ribonucleic acid. An RNA sequence is a sequence of ribonucleotides.

The term "mRNA" refers to messenger ribonucleic acid, which is the fraction of total RNA, which translates to proteins.

The term "mRNA transcript of" refers to the RNA product transcribed from the corresponding gene (DNA) into mRNA, as a first step in the expression and translation to protein.

The term "nucleotide sequence" or "nucleotidic sequence" refers either to a sequence of ribonucleotides (RNA) or a sequence of deoxyribonucleotides (DNA).

The term "protein" indicates at least one molecular chain of amino acids linked through either covalent or non-covalent bonds. The term includes all forms of post-translational protein modifications, for example glycosylation, phosphorylation or acetylation.

The terms "peptide" and "polypeptide" refer to molecular chains of amino acids that represent a protein fragment. The terms "protein" and "peptide" are used indistinguishably.

The phrase "increased levels" means that the levels measured in patients with bladder cancer are higher than the levels measured in a control population of individuals with no history of bladder transitional cell carcinoma.

The term "specificity", refers to the measurement of false positives, where a specificity of 100% means there are no false positives (positive diagnosis of bladder cancer when the patient individual does not in fact have suffer bladder cancer).

The term "sensitivity", as used herein, refers to the measurement of false negatives, where a sensitivity of 100% means there are no false negatives (negative diagnosis of bladder cancer when the patient in fact does have bladder cancer).

The term "antibody" refers to a glycoprotein that exhibits a specific binding activity for a target molecule called an "antigen". The term "antibody" refers to monoclonal or polyclonal antibodies, either intact or fragments derived from them; and includes human antibodies, humanised antibodies and antibodies of non-human origin. The "monoclonal antibodies"

are homogeneous, highly specific antibody populations directed against a single antigenic site or "determinant" of the target molecule. "Polyclonal antibodies" include heterogeneous antibody populations that are directed against different antigenic determinants of the target molecule.

The term "epitope", as it is used in the present invention, refers to an antigenic determinant of a protein, which is the sequence of amino acids of the protein that a specific antibody recognises. Such epitopes may be comprised of a contiguous stretch of amino acids (linear epitope) or of non-contiguous amino acids that are brought into proximity with one another by virtue of the three dimensional folding of the polypeptide chain (discontinuous epitopes).

The term "solid phase", as it is used in the present invention refers to a non-aqueous matrix to which the antibody can bind. Examples of materials for the solid phase include but are not limited to glass, polysaccharides (for example agarose), polyacrylamide, polystyrene, polyvinylic alcohol and silicons. Examples of solid phase forms are the well of a plate or a purification column.

The terms "oligonucleotide primer" and "primer" are used interchangeably in the present invention, and are used to refer to nucleotide sequences, that are complementary to target nucleotide sequences of the FGFR3 or ribl10 genes. Each primer hybridises with its target nucleotide sequence and acts as an initiation site for nucleotide polymerisation catalysed by DNA polymerase, RNA polymerase or reverse transcriptase.

The term "probe", as it is used in the present invention, refers to a nucleotide sequence complementary to a nucleotide sequence derived from the FGFR3 gene that can be used to detect the corresponding nucleotide sequence derived from the FGFR3 gene.

The term "therapeutic target" refers to nucleotide or peptide sequences against which a drug or therapeutic compound can be designed and clinically applied.

The term "antagonist" refers to any molecule that inhibits the biological activity of the antagonised molecule. Examples of antagonistic molecules include, among others, proteins, peptides, variations of natural peptide sequences and small organic molecules (with a molecular weight usually, but not limited to, less than 500 Daltons).

The present invention is based on the discovery that both gene expression of FGFR3, and the concentration of the FGFR3 protein are increased in bladder transitional cell carcinoma, and that the proliferation of bladder tumour cell lines is inhibited when they are treated with a specific antibody raised against the FGFR3 protein.

Therefore, the present invention first of all provides an in vitro method that comprises:
a) the detection and/or quantification of the FGFR3 protein, of the mRNA of the FGFR3 gene, or of the corresponding cDNA in a sample of an individual, and
b) the comparison of the amount of FGFR3 protein, of the mRNA of the FGFR3 gene or of the corresponding cDNA detected in a sample of an individual, with their normal reference values.

Said in vitro method is employed to detect the presence of the bladder transitional cell carcinoma in an individual, to determine the stage or severity of this cancer in an individual or to monitor the effect of the therapy administered to the individual with this cancer.

The method provided by the present invention is highly sensitive and specific and is based on the fact that subjects or individuals diagnosed with bladder transitional cell carcinoma, present high levels of mRNA transcribed from the FGFR3 gene (elevated levels of expression of the FGFR3 gene) or elevated levels of the protein coded by the FGFR3 gene (protein FGFR3), in comparison with the corresponding levels in samples from subjects without a clinical history of this cancer.

The present method comprises a step in which a sample is obtained from the individual. Different liquid samples can be used such as: urine, blood, plasma, serum, pleural fluid, ascitic fluid, synovial fluid, bile, semen, gastric exudate or cerebrospinal fluid. The sample can also consist of bladder that can be obtained by any conventional method, preferably by cystoscopy. Samples can be obtained from subjects previously diagnosed or not diagnosed with transitional cell carcinoma of the bladder; or from a subject receiving treatment, or who has previously received treatment for a cancer, especially for bladder transitional cell carcinoma.

The present method also comprises a step for extraction of the sample, either to obtain an extract of proteins or to obtain an extract of total RNA. One of these two extracts provides the working material for the next phase. The extraction protocols for total protein or total RNA are well known those skilled in the art (Chomczynski P. et al., Anal. Biochem., 1987, 162: 156; Chomczynski P., Biotechniques, 1993, 15: 532). Any conventional assay can be used in the context of the invention to detect a bladder transitional cell carcinoma, provided that it measures in vitro the levels of mRNA transcribed from the FGFR3 gene or its complementary cDNA, or the concentration of the protein FGFR3, in samples collected from individuals to be studied and control individuals.

Therefore, this invention provides a method to detect the presence of a bladder transitional cell carcinoma in an individual, to determine the stage or severity of this cancer in an individual, or to monitor the effect of the therapy administered to an individual who presents this cancer, based either on measuring the levels of the FGFR3 protein or on measuring the level of expression of the FGFR3 gene.

If the aim is to detect and/or quantify the FGFR3 protein, the method of the invention comprises a first step in which the protein extract of the sample is placed in contact with a composition of one or more specific antibodies against one or more epitopes of the FGFR3 protein and a second step to quantify the complexes formed by antibodies and the FGFR3 protein.

There is a wide range of immunological assays available to detect and quantify formation of specific antigen-antibody complexes; numerous competitive or non-competitive protein-binding assays have been described previously and a large number of these are available commercially. Hence, the FGFR3 protein can be quantified with antibodies such as, for example: monoclonal antibodies, polyclonal antibodies, either intact or recombinant fragments of these, combibodies and Fab or scFv fragments of antibodies, specific for the FGFR3 protein; these antibodies are human, humanised or of animal origin. The antibodies used in these assays can be labelled or unlabelled; the unlabelled antibodies can be used in agglutination assays; the labelled antibodies can be used in a wide range of assays. Marker molecules that can be used to label antibodies include radionuclides, enzymes, fluorophores, chemoluminescent reagents, enzymatic substrates or cofactors, enzymatic inhibitors, particles, colorants and derivatives. There are a wide variety of assays well known to those skilled in the art that can be used in the present invention, which use unlabelled antibodies (primary antibody) and labelled antibodies (secondary antibodies); these techniques include but are not limited to the western-blot or western transfer, ELISA (Enzyme-Linked immunosorbent assay), RIA (Radioimmunoassay), Competitive EIA (Competitive enzyme immunoassay), DAS-ELISA (Double antibody sandwich-ELISA), immunocytochemical and immunohistochemical techniques, techniques based on the use of biochips or protein microarrays that include specific antibodies or colloidal precipitation in formats such as dipsticks. Other ways to detect and quantify the FGFR3 protein include affinity chromatography techniques, ligand binding assays or lectin binding assays. The preferred embodiment of this aspect of the invention is a double antibody sandwich ELISA (DAS-ELISA). In this immunoassay any antibody, or combination of antibodies can be used, that are specific against one or more epitopes of the FGFR3 protein. As an example of one of the many possible formats of this assay, a monoclonal or polyclonal antibody, or a fragment of this antibody, or a combination of these antibodies that recognise one or more epitopes of the FGFR3 protein are attached to the surface of a solid phase support and placed in contact with the sample to be analysed and incubated for a specific time and in appropriate conditions to form the antigen-antibody complexes. After washing in appropriate conditions to eliminate non-specific complexes, an indicator reagent, consisting in a monoclonal or polyclonal antibody, or a fragment of this antibody, or a combination of these and which recognises one or more epitopes of the target FGFR3 protein, bound to a signal generating molecule, is incubated with the antigen-antibody complexes in appropriate conditions of time and temperature. The presence of the FGFR3 protein in the sample to be analysed is detected and, if present, quantified and the signal generated is measured. The amount of FGFR3 protein present in the sample to be analysed is proportional to this signal.

When the aim is to detect and/or quantify mRNA or the cDNA corresponding to the FGFR3 gene and not the protein, the method of the invention to detect the susceptibility of an individual to develop transitional cell carcinoma of the bladder in vitro has several different steps. Hence, after obtaining the sample and extracting the total RNA, the method of the invention for the detection of the mRNA or of the corresponding cDNA of the FGFR3 gene, comprises a first step of amplification of the extract of total RNA or the corresponding cDNA synthesised by reverse transcription from the mRNA and a second step of quantification of the amplification product of mRNA or of the cDNA of the FGFR3 gene. One example of mRNA amplification consists in reverse transcription (RT) of the mRNA into cDNA, followed by Polymerase Chain Reaction (PCR), using oligonucleotide primers, using the primer sequences SEQ ID NO.1 and SEQ ID NO. 2. PCR is a technique for the amplification of a specific nucleotide sequence (target) contained in a mixture of nucleotide sequences. In PCR, an excess of a pair of oligonucleotide primers is used that hybridise with complementary strands of the target nucleotide sequence. After this, an enzyme with polymerase activity (DNA Polymerase) extends each primer, using the target nucleotide sequence as a template. The extension products are, therefore, converted into target sequences, after dissociation of the original strand. New primer molecules hybridise and are extended by the polymerase. The cycle is repeated to exponentially increase the number of target sequences. This technique is described in the U.S. Pat. No. 4,683,195 and U.S. Pat. No. 4,683,202. For detection of FGFR3 gene expression, total RNA was obtained from transurethral resection biopsies (TURB) from control subjects without transitional cell carcinoma of the bladder and from biopsies of patients that were clinically typed after resection and presented transitional cell carcinoma of the bladder. After DnaseI treatment 1 µg of each RNA sample was reverse transcribed to give first strand cDNA using Superscript II Reverse transcriptase (Invitrogen, Paisley, UK). One microlitre of an 1:40 dilution of this reaction was used for PCR amplification of a 200 bp fragment of the FGFR3 gene under the following conditions: 25 µl reactions containing 1 µl of 1:40 dilution of cDNA reactions, 3 µl of 6 µM of each primer, 0.5 µl of 10 mM dNTPs, 2.5 µl of 10×PCR buffer, 3 µl of 25 mM $MgCl_2$ and 1 unit of Taq Gold polymerase (Applied Biosystems, Foster City, Calif., USA). The amplification conditions used consisted of: 94° C. for 10 min (denaturation), followed by 40 cycles of 94° C. for 30 sec, 50 C for 30 sec, 72° C. for 1 min 30 sec. and a final extension at 72° C. for 10 min. Many methods have been described previously to detect and quantify amplification products by PCR of which any of these can be used in the present invention. In a preferred method of the invention, the amplified product is detected by agarose gel electrophoresis as follows: five microliters of amplification product are separated by agarose gel electrophoresis at a concentration of 2% agarose, in a Tris-Borate-EDTA (TBE) buffer at 100 volts direct current for one hour. After electrophoresis the gel is stained with ethidium bromide and the amplification product is observed when the gel is illuminated with ultraviolet (uv) light. As an alternative to staining, a preferred method is to transfer the amplified product to a nylon membrane by Southern blotting or Southern transfer techniques to be detected with a specific cDNA probe of the FGFR3 gene, appropriately labelled. In another embodiment, mRNA detection is performed following electrophoretic separation of mRNA by transferring the mRNA to a nylon membrane using transfer techniques such as northern-blot or northern transfer and detecting it with specific RNA probes or of the corresponding cDNA of the FGFR3 gene. In one specific embodiment of this aspect of the invention, amplification and quantification of the mRNA corresponding to the FGFR3 gene, is carried out by quantitative RT-PCR in real time (Q-PCR).

The final step of the method of the invention to detect in vitro the presence of the cancer in a sample from an individual comprises comparing the amount of protein FGFR3, the amount of mRNA of the FGFR3 gene or the amount of the corresponding cDNA, detected in a sample of an individual, with the amount of protein FGFR3, the amount of mRNA of the FGFR3 gene, the amount of corresponding cDNA, detected in the samples of control subjects or in previous non-tumorous samples of the same individual or with normal reference values.

In another aspect, the invention also provides a method in vitro to identify and evaluate the efficacy of therapeutic agents against bladder transitional cell carcinoma that comprises:

a) placing into contact a culture of bladder tumour cells, with the candidate compound, in the appropriate conditions and for the time required for these to interact, b) detection and quantification of the expression levels of the FGFR3 gene or the FGFR3 protein or both, and c) comparing these expression levels with those of a control culture of tumour cells not treated with the candidate compound.

Quantification of the expression levels of the FGFR3 gene or the FGFR3 protein is performed in a similar manner to that described in the method of the invention to detect in vitro the presence of a cancer of the pancreas, especially of a bladder transitional cell carcinoma, in an individual.

When an agent reduces the expression levels of the FGFR3 gene or reverses the effects of high expression of this gene, preferably reducing the levels of cellular proliferation, this agent becomes a candidate for cancer therapy, in particular for bladder transitional cell carcinoma.

Another aspect of this invention refers to the use of nucleotide or peptide sequences derived from the FGFR3 gene, in methods to screen for, identify, develop and evaluate the efficacy of therapeutic compounds against bladder transitional cell carcinoma. It is noteworthy, the recent importance given to screening methods based on the competitive or non-competitive binding of the potential therapeutic molecule to the therapeutic target.

A further aspect of this invention refers to the use of nucleotide or peptide sequences derived from the FGFR3 gene to detect the presence of a carcinoma, especially of a bladder transitional cell carcinoma, to determine the stage or severity of this cancer in the individual or to monitor the effect of the therapy administered to an individual with this cancer.

Another aspect of this invention consists in providing agents which inhibit expression and/or activity of the FGFR3 protein. These agents, which can be identified and evaluated according to the present invention, can be selected from the group formed by:
 a) an antibody, or combination of antibodies, specific against one or more epitopes present in the FGFR3 protein, preferably a human or humanised monoclonal antibody. These can also be a fragment of antibody, a single chain antibody or an anti-videotape antibody,
 b) cytotoxic agents, such as toxins, molecules with radioactive atoms or chemotherapeutic agents, including, but not limited to, small organic and inorganic molecules, peptides, phosphopeptides, antisense molecules, ribozymes, siRNAs, triple helix molecules etc. that inhibit expression and/or activity of the FGFR3 protein, and
 c) compounds that are antagonists of the FGFR3 protein, that inhibit one or more of the functions of the FGFR3 protein A further aspect of the present invention is a pharmaceutical composition that includes a therapeutically effective amount of one or several of the previously mentioned agents together with one or more excipients and/or transporter substances. Also, this composition can contain any other active ingredient that inhibits the function of the FGFR3 protein. The excipients, transporter compounds and auxiliary substances must be pharmaceutically and pharmacologically tolerated so that they can be combined with other components of the formulation or preparation and not have any adverse effects on the organism treated. The pharmaceutical compositions or formulations include those that are suitable for oral or parenteral administration (including subcutaneous, intradermal, intramuscular or intravenous), although the best route of administration depends on the patient's condition. Formulations can also be in the form of single doses. Formulations are prepared according to well known pharmacological methods. The amounts of active substances to be administered vary depending on the characteristics of the therapy.

A final aspect of the present invention consists in a kit for carrying out the present invention. Thus, an embodiment of the present invention provides a kit that comprises an anti-FGFR3 antibody and a carrier in suitable packing. In another embodiment the kit of the invention comprises a primer pair designed to specifically amplify a nucleic acid having a sequence that is specific of the FGFR3 gene. The sequence of the primer pair can be determined from the sequence of the corresponding FGFR3 gene by employing bioinformatic tools. The sequence of said primer pair is preferably selected from SEQ ID NO.1 and SEQ ID NO.2. These kits can be employed to detect the presence of the bladder transitional cell carcinoma in an individual, to determine the stage or severity of this cancer in an individual or to monitor the effect of the therapy administered to the individual with this cancer.

The following examples serve to illustrate the invention.

Example 1

Differential Analysis of the Expression of the FGFR3 Gene in Samples of Bladder Tissue, Using Human Genome U95 DNA Arrays 1.1. Materials and Methods Microarrays. GeneChip Test 3 (Affymetrix, Santa Clara) microarrays were used, that permit the quality of RNA to be tested before analysing expression with the GeneChip Human Genome U95A array (Affymetrix, Santa Clara), which represents 12,000 complete sequences of annotated genes; the FGFR3 gene is represented in the microarray by the set of probes 31805_at of Affymetrix, which are sense oligonucleotides 25 nucleotides long, designed on the basis of the Hs.1420 sequence of Unigene, or N. Acc. M64347 of GeneBank (Table 1).

TABLE 1

Description of the probes corresponding to the set of probes 31805_at.

| Consecutive order of probes | Region of the interrogated reference sequence | Probe sequence (5'-3') | Probe position in mRNA sequence |
| --- | --- | --- | --- |
| 1 | 3511 | SEQ ID NO: 3 | 3227 |
| 2 | 3625 | SEQ ID NO: 4 | 3340 |
| 3 | 3633 | SEQ ID NO: 5 | 3348 |
| 4 | 3663 | SEQ ID NO: 6 | 3378 |
| 5 | 3684 | SEQ ID NO: 7 | 3399 |
| 6 | 3716 | SEQ ID NO: 8 | 3431 |
| 7 | 3722 | SEQ ID NO: 9 | 3437 |
| 8 | 3821 | SEQ ID NO: 10 | 3536 |
| 9 | 3825 | SEQ ID NO: 11 | 3540 |
| 10 | 3831 | SEQ ID NO: 12 | 3546 |
| 11 | 3861 | SEQ ID NO: 13 | 3576 |
| 12 | 3873 | SEQ ID NO: 14 | 3588 |
| 13 | 3891 | SEQ ID NO: 15 | 3606 |
| 14 | 3903 | SEQ ID NO: 16 | 3618 |
| 15 | 3933 | SEQ ID NO: 17 | 3648 |
| 16 | 4005 | SEQ ID NO: 18 | 3720 |

Samples

The samples studied were from transurethral resection biopsies (TURB) from control non-neoplastic individuals (7 cases, 2 containing muscular layer and 5 without muscular layer) and from biopsies of patients that were clinically typed after resection and presented transitional cell bladder carcinoma (22 cases) in one of the following stages: Nine cases were low-grade non-invasive carcinomas (pTaG1), seven cases were high-grade carcinomas with lamina propria invasion (pT1G3), and six cases were high-grade muscle invading carcinomas (pT2G3). Every sample was histologically typed (grade and stage) in the Pathological Anatomy Department of the University Hospital Marques de Valdecilla, the same hospital where the samples were obtained following the guidelines of the Helsinki Declaration. Fresh tissue was immediately frozen in liquid nitrogen after extraction and stored at −80° C. until processing.

For each stage of tumour the following samples were analysed:
Control tissue without muscular layer; 5 samples
Control tissue with muscular layer: 2 samples
TaG1: 9 samples
T1G3: 7 samples
T2G3: 6 samples GeneChip Gene Expression Analysis Analysis was done with total RNA from individual subjects and with equimolar mixtures (pools) of total RNAs from either healthy individuals or from patients suffering the same stage of bladder transitional cell carcinoma. (Table 2).

TABLE 2

Description and number of samples comprised in each pool

| | Epithelial Control | Muscular Control | Ta G1 | T1 G3 | T2 G3 |
|---|---|---|---|---|---|
| Samples | 3*(pC1)[a], 2 (pC3) | 2 (pC2) | 1, 4(pTa.1)[b], 4 (pTa.2) | 1, 2(pT1.1)[c], 4 (pT1.2) | 1, 2(pT2.1)[d], 3 (pT2.2) |

*number of samples comprising each pool.
[a]pC: pool of control sample. Example: 3(pC1) = pool 1 with 3 control samples.
[b]pTa: pool of Ta tumour samples. Example: 4(pTa.1) = pool 1 with 4 TaG1 samples.
[c]pT1: pool of T1 tumour samples. Example: 2(pT1.1) = pool 1 with 2 T1G3 samples.
[d]pT2: pool of T2 tumour samples. Example: 2(pT2.1) = pool 1 with 2 T2G3 samples.

cRNA Synthesis

Total RNA from each biopsy was obtained by homogenising the tissue in TRIzol® Reagent (Life Technologies), following the supplier's recommendations. The resulting total RNA was cleaned with the Rneasy kit (QIAGEN) (Chomczynski P. et al., Anal. Biochem., 1987, 162: 156; Chomczynski P., Biotechniques, 1993, 15: 532). Of each preparation of total RNA, 10 μg were used as starting material for synthesis of the first strand cDNA with the reverse transcriptase enzyme SuperScript™ II RNase (Life Technologies), using as a primer an oligo-dT oligonucleotide carrying the T7 phage RNA polymerase promoter sequence. Second strand cDNA was synthesised using the enzymes DNA polymerase I of *E. coli* (Invitrogen Life Technologies), DNA ligase of *E. coli* (Invitrogen Life Technologies), RNAse H of *E. coli* (Invitrogen Life Technologies), and DNA polymerase of phage T4 (Invitrogen Life Technologies). The biotin labelled cRNA was synthesised using the ENZO BioArray™ HighYield™ Transcript Labelling Kit (Enzo Diagnostics Inc). After in vitro transcription, the unincorporated nucleotides were eliminated using the RNeasy columns (QIAGEN).

Array Hybridization and Scanning

A total of 15 μg of each biotinylated cRNA were fragmented at 94° C. for 35 minutes in a buffer solution containing 40 mM Tris-Acetate (pH 8.1), 100 mM potassium acetate and 30 mM magnesium acetate. The fragmented cRNA was mixed with hybridization buffer (100 mM MES, 1M NaCl, 20 mM EDTA, 0.01% Tween 20) and heated to 990 for 5 minutes and then to 45° for 5 minutes, after which it was loaded in the Affymetrix array. The first array in which the hybridization was carried out was Test 3 of Affymetrix. With this array the quality of RNA can be tested before analysing expression in the Affymetrix® GeneChip® Human Genome 95 A (HG-U95A).

For hybridization, arrays were incubated in a rotary incubator at 45° for 16 hours with a constant rotation of 60 rpm.

Washing and staining of each array was done in the Affymetrix® fluid station. A washing and staining programme was used that included:

10×2 washing cycles with SSPE-T 6× (0.9 m NaCl, 60 mM NaH$_2$PO$_4$, 6 mM EDTA, 0.01% Tween 20) at 25° C., 4×15 cycles with 0.1 mM MES, 0.1M NaCl, 0.01% Tween 20 at 50° C., Staining with biotinylated cRNA with a phycoerythrin streptavidin conjugate (10 μg/ml Molecular Probes)

10×4 washing cycles with SSPE-T at 25° C.,

Staining an anti-streptavidin conjugate for 10 minutes

Staining a phycoerythrin-streptavidin conjugate (1 mg/ml, Molecular Probes) for 10 minutes 15×4 washing cycles with SSPE-T at 30° C.

Arrays were scanned at 560 nm using a confocal microscope that uses laser emission (Agilent GeneArray Scanner). Analysis of intensity readings was done with the Microarray Suite 5.0 software. For comparison of arrays these were scaled to a total intensity of 100.

1.2. Results

Analysis of differential expression of the FGFR 3 gene in neoplastic samples compared to controls was performed from the Affymetrix microarray data. The following parameters were considered in the analysis: detection (classification of the gene as; present (P), absent (A) or marginal (M), in each sample); Change (indicating an increase (I), decrease (D) or no change (NC) for each sample); and the Signal Log Ratio (SLR; indicating the change in expression levels between a base line control and each sample). This change is expressed as the $\log_2$ of the ratio (base 2 logarithm of the fold change or number of times that gene expression, is increased or decreased in the tumour sample compared to the non neoplastic control sample). We considered a SLR of 1 or −1 (representing respectively a fold change increase or decrease of 2) as a significant value for gene expression change Compared to controls expression levels of FGFR3 were increased more than 8-fold (SLR>3) in pTaG1 and pT1G3 carcinomas and more than 4-fold (SLR>2) in T2G3 carcinomas (Table 3).

TABLE 3

Microarray hybridization results for Fibroblast growth factor receptor 3 (FGFR3) based on Affymetrix MAS5.0 software. (N. Acc. M64347)

| Control sample signal | Control sample detection | Detection pTaG1 stage | SLR TaG1 vs Control | TaG1 Change | Comparison |
|---|---|---|---|---|---|
| 132.7 | P | P | 2.5 | I | pTa.1 vs pC1 |
| 67.7 | A | P | 4.2 | I | pTa.1 vs pC2 |
| 28.1 | A | P | 4.4 | I | pTa.1 vs pC3 |
| 132.7 | P | P | 1 | I | pTa.2 vs pC1 |
| 67.7 | A | P | 3 | I | pTa.2 vs pC2 |
| 28.1 | A | P | 3.5 | I | pTa.2 vs pC3 |
| SLR Average | | | 3.1 | I | |

| Control sample signal | Control sample detection | Detection G3 stage | SLR T1G3 vs. Control | T1G3 Change | Comparison |
|---|---|---|---|---|---|
| 132.7 | P | P | 1.7 | I | pT1.1 vs. pC1 |
| 67.7 | A | P | 3.9 | I | pT1.1 vs. pC2 |
| 28.1 | A | P | 3.7 | I | pT1.1 vs. pC3 |
| 132.7 | P | P | 2 | I | pT1.2 vs. pC1 |
| 67.7 | A | P | 4.1 | I | pT1.2 vs. pC2 |
| 28.1 | A | P | 4.4 | I | pT1.2 vs. pC3 |
| SLR Average | | | 3.3 | I | |

| Control sample signal | Control sample detection | Detection T2 G3 stage | SLR T2G3 vs Control | T2G3 Change | Comparison |
|---|---|---|---|---|---|
| 132.7 | P | P | 1.4 | I | pT2.1vspC1 |
| 67.7 | A | P | 3.3 | I | pT2.1vspC2 |
| 28.1 | A | P | 3.2 | I | pT2.1vspC3 |
| 132.7 | P | P | 0.6 | I | pT2.2vspC1 |
| 67.7 | A | P | 2.4 | I | pT2.2vspC2 |

TABLE 3-continued

Microarray hybridization results for Fibroblast growth factor receptor 3 (FGFR3) based on Affymetrix MAS5.0 software. (N. Acc. M64347)

| 28.1 | A | P | 2.7 | I | pT2.2vspC3 |
|------|---|---|-----|---|------------|
| SLR Average | | | 2.26 | I | |

1.3. Discussion

Differential expression analysis of FGFR3 gene confirmed that compared to controls expression levels of fgfr3 were increased more than 8-fold (SLR>3) in pTaG1 and pT1G3 carcinomas and more than 4-fold (SLR>2) in T2G3 carcinomas (Table 3).

Example 2

Differential Analysis of Expression of the FGFR3 Protein in Bladder Tissue Samples Using the Western Blot Technique with Specific Antibodies 2.1. Materials and Methods Samples:

Samples were obtained form transurethral resection biopsies (TURB). In this part of the study we analysed three urinary bladder samples from healthy individuals (samples 46, 55 and 63), six low-grade superficial carcinomas (pTaG1) (samples 48, 49, 50, 53, 56 and 59), three high-grade lamina propria invasive carcinomas (pT1G3) (samples 57, 61 and 67) four high-grade muscle-invading carcinomas (pT2G3) (samples 47, 51, 58 and 60) and two samples of unknown grade (samples 54 and 62). The samples were from different patients than those used for the microarray analysis. Fresh tissue was immediately frozen in liquid nitrogen after extraction and stored at −80° C. until used for extraction of protein. All the samples used in this study were obtained by surgical transurethral resection performed in the Urology Service of the University Hospital Marques de Valdecilla (Santander, Spain); samples were histologically typed in the Anatomical Pathology department of the same hospital. The precepts of the Helsinki Declaration were followed throughout.

Protein Extraction

The frozen tissue samples were homogenised in mortars with liquid nitrogen and the pulverized product was added to RIPA B buffer (sodium phosphate 20 mM [pH 7.4], NaCl 150 mM, Triton X-100 1%, EDTA 5 mM) as well as a proteases inhibitor cocktail (Roche Diagnostics Inc., Mannheim, Germany).

Western Blotting Experiments

Protein samples (20 μg of total protein) were mixed with SDS-PAGE gel loading buffer supplemented with 5% β-mercaptoethanol and incubated at 100° C. for 5 min, before being loaded on 6% polyacrylamide gel. Following electrophoresis proteins were transferred to nitrocellulose membranes. Duplicate gels were run and blotted. One membrane was probed with antibodies raised against the FGFR3 protein (Santa Cruz Biotech. Inc., Santa Cruz, Calif., USA.) while the second membrane was probed with antibody raised against actin (Amersham, Little Chalfont, UK) as a control for protein loading. Finally, membranes were hybridised with a secondary antibody conjugated with peroxidase (Amersham) and the chemoluminescent signal was detected using the ECL system (Amersham) with high performance chemiluminescence film (Hyperfilm ECL, Amersham).

2.2. Results.

Expression of the FGFR3 Protein in Bladder Transitional Cell Carcinoma

FGFR3 protein expression in healthy samples (n=3) and tumours (n=15) was investigated by western blotting. The results are shown in FIG. 1 and table 4. As the results show the FGFR3 protein was not detected in the control samples analysed. With regard to the tumour samples FGFR3 was present in 11 of the 15 samples analysed (73%), being higher in low-grade tumours (83%) and high-grade tumours that infiltrated the lamina propria (100%).

The receptor appeared in the form of several immunoreactive bands of distinct molecular weights: Western blot analysis showed bands forming a smear of glycosylated form 135 kDa, corresponding to the fully glycosylated form; 85 kDa corresponding to the intracellular non-glycosylated form and several bands of intermediate molecular weight corresponding with the different FGFR3 glycosylation states In addition some low molecular weight (50 kDa) immunoreactive bands were also present, which may represent proteolytic degradation products of the protein (FIG. 1).

TABLE 4

FGFR-3 protein expression.

| Sample | N | Samples positive for FGFR3 | % Of samples positive |
|--------|---|----------------------------|----------------------|
| normal bladder | 3 | 0 | 0 |
| TaG1 | 6 | 5 | 5 (83%) |
| T1G3 Carcinoma | 3 | 3 | 3 (100%) |
| T2G3 Carcinoma | 4 | 2 | 2 (50%) |
| Unclassified | 2 | 1 | 2 (100%) |

2.3. Discussion

The results obtained shown that the FGFR3 protein, which is undetectable in normal bladder tissue is expressed in the majority of the bladder transitional cell carcinoma samples. In some these tumours the level of FGFR3 protein is singularly high. The sensitivity of the detection system is 73% with 100% specificity.

Example 3

In Vitro Inhibition of Bladder Tumoral Cell Line Proliferation by Specific Antibodies Against the FGFR3 Protein 3.1. Materials and Methods Culture Cell Lines:

The RT112 human bladder carcinoma epithelial cell line was obtained from the German Collection of Microorganisms and Cell Cultures (Braunschweig, RFA). RT-112 cells were grown in RPMI medium, supplemented with 10% foetal bovine serum (FBS) and 2 mM glutamine, except where otherwise stated. Tissue culture reagents were obtained from Invitrogen (Paisley, UK).

Preparation of Protein Lysates:

Cells from a 10 cm plate were washed twice with cold phosphate buffered saline (PBS), pH 7.4 and collected in 0.5 ml of RIPA B. Samples were centrifuged at 15000×g for 10 min at 4° C. to pellet cellular debris. The supernatant was kept and the protein concentration was measured using the Bradford protein assay (BioRad, Hercules, Calif., USA) (Molina, M. A. et al., Cancer Res., 1999, 59: 4356-4362).

Protein samples (20 μg of total protein) were mixed with SDS-PAGE gel loading buffer supplemented with 5% of β-mercaptoethanol and incubated at 100° C. for 5 min, before being loaded on 6% polyacrylamide gel. Following electrophoresis proteins were transferred to nitrocellulose membranes. Duplicate gels were run and blotted. One membrane was probed with antibodies raised against the FGFR3 protein (Santa Cruz Biotech. Inc., Santa Cruz, Calif., USA) while the second membrane was probed with an antibody raised against actin (Amersham) as a control for protein loading. Finally, membranes were hybridised with a secondary antibody conjugated with peroxidase (Amersham, Little Chalfont, UK) and the chemoluminescent signal was detected using the ECL system (Amersham) with high performance chemiluminescence film (Hyperfilm ECL, Amersham).

Cell Proliferation Assays:

Experiments were performed to evaluate the effect of a mouse monoclonal antibody raised against human FGFR3 on the proliferation of RT-112 cells by comparing the proliferation rate of cells grown in the presence of the antibody raised against FGFR3 with proliferation in the presence of a control antibody raised against mouse β2-microglobulin (Santa Cruz). The preservative sodium azide was first removed from the antibody solutions by washing and concentrating the antibodies three times with PBS using a 10-kDa Centricon filtration device (10-kDa MWCO, Millipore CO., Bedford, Mass.), followed by filter sterilization through a 0.2 μm filter previously saturated with Dulbecco's modified Eagle's medium (DMEM) and 10% FBS. Antibodies were diluted in culture media. RT-112 cells were seeded in a 96-well plate at a density of $2\times10^3$ cells per well (0.2 ml) in RPMI medium containing 10% foetal bovine serum (FBS). Cells were allowed to attach to the wells for 24 hours before the RPMI medium was removed and replaced by fresh RPMI containing antibodies at concentrations of: 0, 0.02, 0.2, 2 and 20 μg/ml. The growth rate was estimated after 24 and 48 hours by measuring the formation of reduced MTT (methylthiazoltetrazolium) (Sigma Chemical Co., St Louis, USA) Briefly, after 1 and 2 days incubation, media was removed and replaced by 100 μl of 1 mg/ml MTT in RPMI medium containing 10% FBS. To provide the blanks for absorbance readings some control wells of medium alone were included. The plate was incubated for 30 to 60 minutes at 37° C. After the media was removed, 100 μl of DMSO were added to each well. The cells viability was determined by MTT absorbance (550 nm) and extrapolation of the absorbance intensity from a standard curve.

3.2. Results.

Figure 2:
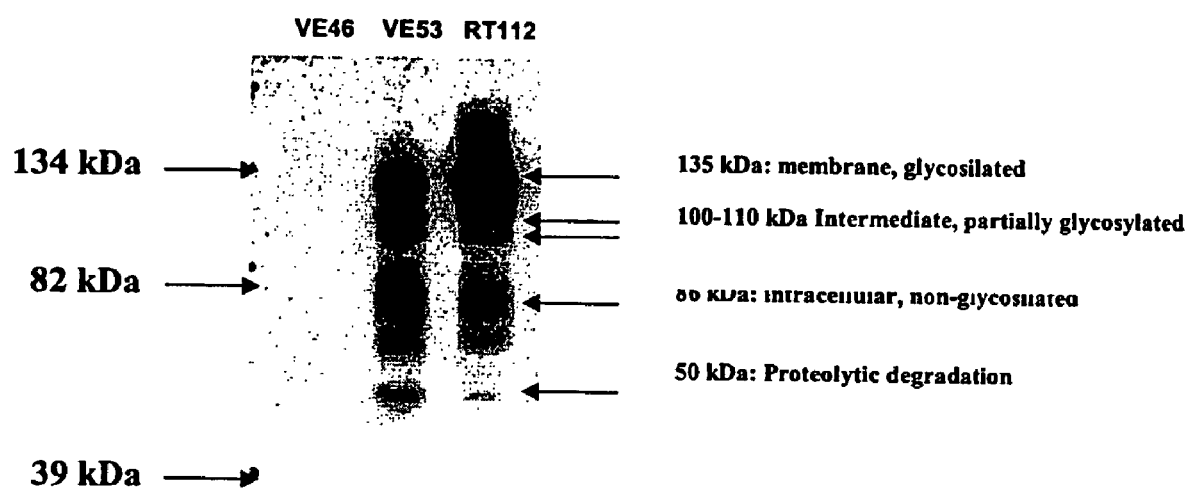
FIG. 2 shows the results of a western blot analysis of the expression of the FGFR3 protein in the bladder transitional cell carcinoma cell line RT-112. Protein extract of normal bladder tissue was used as control (sample 46). Protein extract from a bladder tumour sample was used as positive control (sample 53). For each sample, a total of 20 micrograms of protein was loaded FIG. 3 shoes the effects of anti-FGFR3 (blue bars) and anti-β2 microglobulin (red bars) on bladder transitional cell carcinoma RT-112 cells growth in serum-free media. Cells were seeded in 96-well plates and were treated with antibodies for 24 or 48 h. Growth rate is expressed a comparison between cell lines growth with and without antibody. Each value is calculated from 6 replicas and the vertical lines represent the standard deviation.

Expression of FGFR3 Protein in the Bladder Transitional Cell Carcinoma Cell Line RT-112:

Expression of FGFR3 was tested by western blot analysis, detecting high levels of the receptor (FIG. 2). This appeared in the form of various immunoreactive bands of different molecular weights: 135 kDa corresponding to the fully glycosylated form; 85 kDa corresponding to the intracellular non-glycosylated form and several intermediate bands (100-110 kDa) corresponding to different FGFR3 glycosylation states. In addition lower molecular weight (50 kDa) immunoreactive bands were detected possibly corresponding to proteolytic degradation of the protein.

Figure 3:
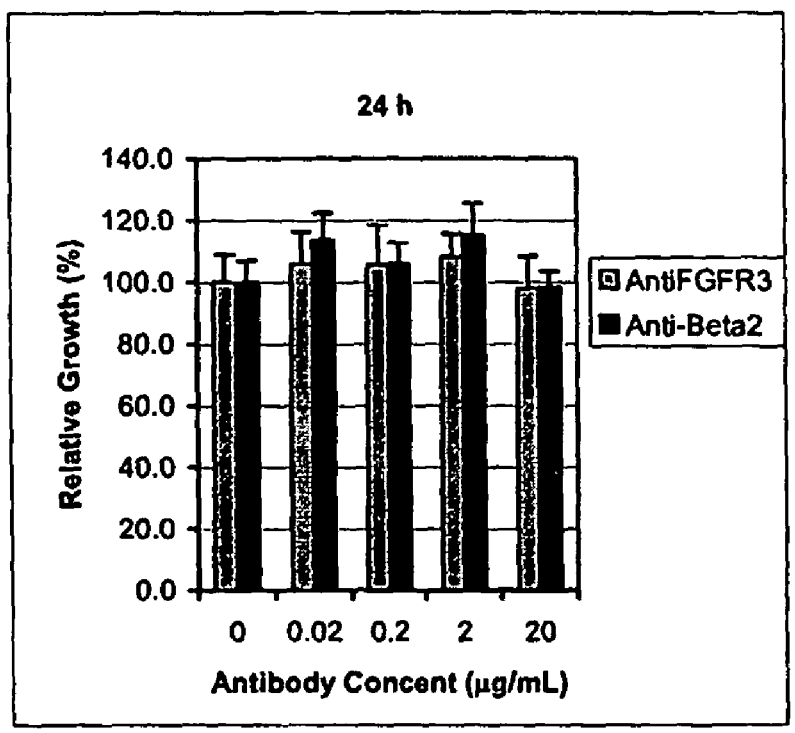
Figure 3:
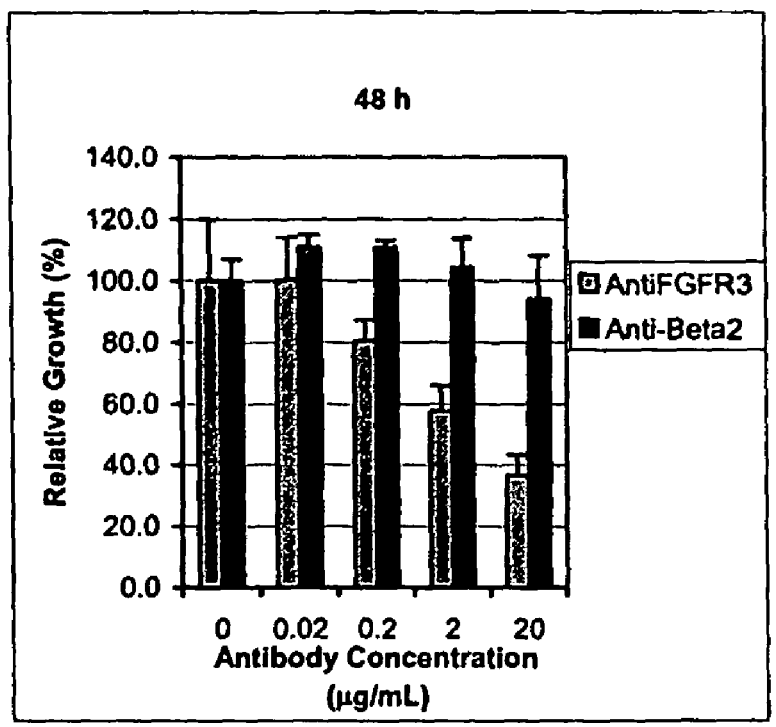

Inhibition of Cell Growth by Antibodies Against FGFR3:

During recent years many antibodies have been described that are directed against extracellular domains of membrane receptors that posses antiproliferative properties. For this reason it was decided to test whether a monoclonal antibody, raised against FGFR3, was capable of inhibiting the growth of a bladder transitional cell carcinoma cell line. For the assay the cell line RT-112 was selected as the only cell line showing detectable levels of the receptor. Assays were performed in serum free media or in media supplemented with 10% foetal bovine serum and cells were incubated for 24 and 48 hours in the presence of antibody for 24 and 48 hours. As a control another monoclonal antibody, obtained from the same source (Santa Cruz Biotechnology) and raised in mice against β2 microglobulin was used As shown in FIG. 3, anti-FGFR3 antibody inhibited proliferation of RT-112 cells in serum free-media after 48 hours while anti-2 microglobulin antibody showed no effect. On the other hand, in 10% FBS supplemented media, none of the antibodies showed a significant effect on proliferation of RT-112 cells.

3.3. Discussion

The results presented in this example show that the expression level of the FGFR3 protein, which is not detectable in normal bladder, is elevated in the bladder carcinoma cell line RT-112. FGFR3 is a membrane glycoprotein that interacts with the FGF family of growth factors triggering a signalling cascade that stimulates cell proliferation (Keegan et al., Oncogene, 1991, 6:2229-2236). This receptor could play a pivotal role in the origin and progression of bladder transitional cell carcinoma.

Treatment of RT-112 cell with a monoclonal antibody directed against the extracellular domain of FGFR3 protein in serum-free media, inhibits cell growth. Different, and not mutually exclusive mechanisms, could explain this effect: the antibody could block receptor binding, or inhibit receptor dimerisation (the step prior to receptor activation), or deplete the concentration of receptor at the plasma membrane.

To summarise, the over-expression of FGFR3 in bladder transitional cell carcinoma and the fact that proliferation of the bladder carcinoma cell line RT-112 is inhibited by a monoclonal antibody raised against FGFR3, suggests that this protein is a promising candidate as a therapeutic target for the development of drugs to treat bladder transitional cell carcinoma; likewise these results show that the antibody against FGFR3 protein could be the active ingredient of one of the drugs developed.

Example 4

Analysis of Protein Expression in Tissue Samples Using Tissue Arrays 4.1. Material and Methods Fixed paraffin-embedded tumour samples from the pathology archives of the Hospital Universitario Marqués de Valdecilla were sectioned and arrayed on glass slides. In total 209 cases of urinary bladder transitional cell carcinoma from transurethral resection biopsies and cystectomy specimens and 20 healthy bladder samples (total: 229) were examined by immunohistochemical staining. All paraffin-embedded donor tissue blocks were sampled with 0.6-mm punchers using a Beecher tissue microarray instrument (Beecher Instruments Inc. Sun Prairie, Wis., USA). Paraffin tissue array blocks containing arrayed core cylinders from 37 pTa, 100 pT1, 72 pT2 and 20 healthy bladder samples were subjected to routine staining with hematoxylin and eosin followed by immunohistochemical staining for the FGFR3 protein. A monoclonal antibody raised against FGFR3 (1:25 dilution; Santa Cruz Biotech. Inc., Santa Cruz, Calif., USA) was used for immunostaining.

Figure 4:
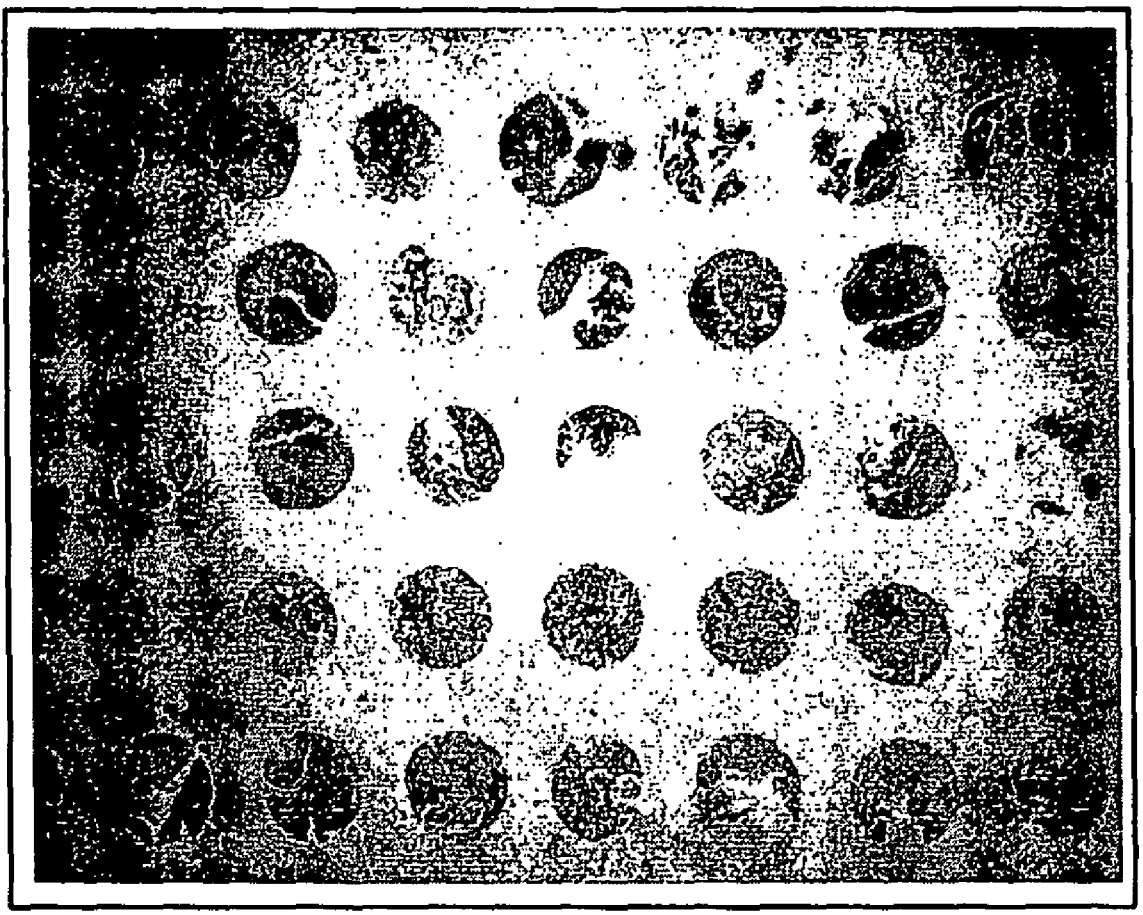
FIG. 4 shows tissue array showing circular sections from bladder tissue biopsies after routine staining with hematoxylin and eosin followed by immunohistochemical staining for the FGFR3 protein.

Briefly, antigen retrieval was performed by boiling sections in citric acid buffer in a pressure cooker for 90 sec. The Dako EnVision™+kit (Dako, Glostrup Denmark) was used as a visualization system according to the manufacturers' instructions, in a Techmate 500-220 automated immunostainer (Biotek, Santa Barbara, Calif., USA). Diaminobenzidine was used as the chromogen (FIG. 4).

Figure 5:
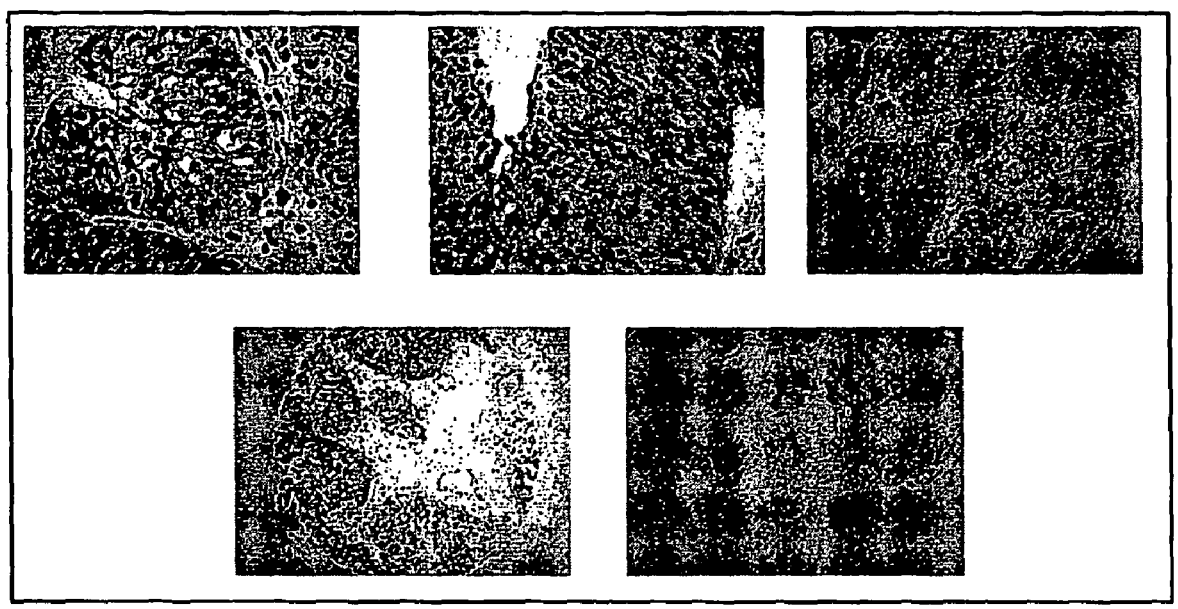
FIG. 5 shows immunohistochemical detection of FGFR3 protein in tissue samples of three stages of bladder transitional cell carcinoma, Ta (A and D), T1 (B), T2 (C) and control healthy bladder. Positive staining of FGFR3 was defined as a coarse cytoplasmic membrane reactivity. Immunohistochemistry was considered negative in cases with weak staining of <5% of the cells.

To reduce interobserver variability in the histopathological evaluation of the antibody-stained specimens three independent pathologists from the Pathological Anatomy Department of the University Hospital Marques de Valdecilla evaluated staining patterns and scoring criteria were agreed. Positive staining of FGFR3 was defined as a coarse cytoplasmic membrane reactivity (FIG. 5). Immunohistochemistry was considered negative in cases where staining was absent or which showed weak staining (<5% of cells in a given section).

4.2. Results

Of the urinary bladder transitional cell carcinoma sections that were analysed immunohistochemically a positive reaction with the antibody specific for FGFR3 was positive in 71.4% of Ta sections, 72% of T1 sections and 49.2% of T2 sections (table 5) compared to the 5% of healthy positive sample. Consistent with previous data the T1 sections classified as high-grade showed a lower percentage of positive sections (table 6) than sections corresponding to lower grades of transitional cell carcinoma of the bladder.

TABLE 5

Description of samples analysed and tissue array results

| Bladder transitional cell carcinoma pT1 grade | Total n° of sections | Useable sections | Positive cases | Negative cases | Null cases | % of positive cases |
|---|---|---|---|---|---|---|
| G1 | 16 | 15 | 15 | | 1 | 100% |
| G2 | 32 | 31 | 24 | 8 | 3 | 77.4% |
| G3 | 24 | 22 | 13 | 10 | 1 | 59.1% |

* Cases that have not been analysed due to the array preparation
** Percentage of positive cases among useable sections

TABLE 6

Results of Immunohistochemical Staining

| | Total n° of samples | Useable sections | Positive cases | Negative cases | Null cases | % of positive cases** |
|---|---|---|---|---|---|---|
| Bladder transitional cell carcinoma pTa | 37 | 36 | 25 | 11 | 1 | 71.4% |
| Bladder transitional cell carcinoma pT1 | 100 | 93 | 67 | 26 | 7 | 72% |
| Bladder transitional cell carcinoma pT2 | 72 | 67 | 33 | 34 | 5 | 49.2% |
| Bladder Healthy tissue | 20 | 20 | 1 | 19 | — | 5% |

* Cases that have not been able to be analysed due to the array preparation
**Percentage of positive cases among useable sections 4.3. Discussion The results presented in this example provide evidence for FGFR3 protein expression in a large number of bladder cancer transitional cell carcinomas (209). Elevated levels of FGFR3 protein expression in cell membranes was predominantly associated with the Ta and T1 stages (mainly superficial tumours) of bladder cancer transitional cell carcinomas. Percentages of positive Ta, T1 and T2 cases correlate well with previous results obtained in western blot analysis of FGFR3 expression in bladder cancer transitional cell carcinoma biopsy samples.

SEQUENCE LISTING

<160> NUMBER OF SEQ ID NOS: 18

<210> SEQ ID NO 1
<211> LENGTH: 20
<212> TYPE: DNA
<213> ORGANISM: Artificial sequence
<220> FEATURE:
<223> OTHER INFORMATION: direct primer designed to amplify, in
      combination with SEQ ID NO:2, cDNA of the fgfr3 gene

<400> SEQUENCE: 1
gacggtttcc agggaggggc                                          20

<210> SEQ ID NO 2
<211> LENGTH: 25
<212> TYPE: DNA
<213> ORGANISM: Artificial sequence
<220> FEATURE:
<223> OTHER INFORMATION: reverse primer designed to amplify, in
      combination with SEQ ID NO:1, cDNA of the fgfr3 gene

<400> SEQUENCE: 2
gtaacagtac agaacgaacc aactg                                    25

<210> SEQ ID NO 3
<211> LENGTH: 25
<212> TYPE: DNA
<213> ORGANISM: Artificial sequence
<220> FEATURE:
<223> OTHER INFORMATION: probe sequence of the 31805_at probe set of
      Affymetrix, the position of said probe in the mRNA sequence of the
      fgfr3 gene being 3227

<400> SEQUENCE: 3
tccaagccta aaaggttgtt aatag                                    25

<210> SEQ ID NO 4
<211> LENGTH: 25
<212> TYPE: DNA
<213> ORGANISM: Artificial sequence
<220> FEATURE:
<223> OTHER INFORMATION: probe sequence of the 31805_at probe set of
      Affymetrix, the position of said probe in the mRNA sequence of the
      fgfr3 gene being 3340

<400> SEQUENCE: 4
attttttgga cttcaaagca agctg                                    25

<210> SEQ ID NO 5
<211> LENGTH: 25
<212> TYPE: DNA
<213> ORGANISM: Artificial sequence
<220> FEATURE:
<223> OTHER INFORMATION: probe sequence of the 31805_at probe set of
      Affymetrix, the position of said probe in the mRNA sequence of the
      fgfr3 gene being 3348

<400> SEQUENCE: 5
gacttcaaag caagctggta ttttc                                    25

<210> SEQ ID NO 6
<211> LENGTH: 25
<212> TYPE: DNA
<213> ORGANISM: Artificial sequence
<220> FEATURE:
<223> OTHER INFORMATION: probe sequence of the 31805_at probe set of
      Affymetrix, the position of said probe in the mRNA sequence of the
      fgfr3 gene being 3378

<400> SEQUENCE: 6
aattcttcta attgctgtgt gtccc                                    25

<210> SEQ ID NO 7
<211> LENGTH: 25
<212> TYPE: DNA
<213> ORGANISM: Artificial sequence
<220> FEATURE:
<223> OTHER INFORMATION: probe sequence of the 31805_at probe set of
      Affymetrix, the position of said probe in the mRNA sequence of the
      fgfr3 gene being 3399

<400> SEQUENCE: 7

```
tcccaggcag ggagacggtt tccag                                          25

<210> SEQ ID NO 8
<211> LENGTH: 25
<212> TYPE: DNA
<213> ORGANISM: Artificial sequence
<220> FEATURE:
<223> OTHER INFORMATION: probe sequence of the 31805_at probe set of
      Affymetrix, the position of said probe in the mRNA sequence of the
      fgfr3 gene being 3431

<400> SEQUENCE: 8
ccggccctgt gtgcaggttc cgatg                                          25

<210> SEQ ID NO 9
<211> LENGTH: 25
<212> TYPE: DNA
<213> ORGANISM: Artificial sequence
<220> FEATURE:
<223> OTHER INFORMATION: probe sequence of the 31805_at probe set of
      Affymetrix, the position of said probe in the mRNA sequence of the
      fgfr3 gene being 3437

<400> SEQUENCE: 9
ctgtgtgcag gttccgatgt tatta                                          25

<210> SEQ ID NO 10
<211> LENGTH: 25
<212> TYPE: DNA
<213> ORGANISM: Artificial sequence
<220> FEATURE:
<223> OTHER INFORMATION: probe sequence of the 31805_at probe set of
      Affymetrix, the position of said probe in the mRNA sequence of the
      fgfr3 gene being 3536

<400> SEQUENCE: 10
cacttcttac gcaatgcttc tagag                                          25

<210> SEQ ID NO 11
<211> LENGTH: 25
<212> TYPE: DNA
<213> ORGANISM: Artificial sequence
<220> FEATURE:
<223> OTHER INFORMATION: probe sequence of the 31805_at probe set of
      Affymetrix, the position of said probe in the mRNA sequence of the
      fgfr3 gene being 3540

<400> SEQUENCE: 11
tcttacgcaa tgcttctaga gtttt                                          25

<210> SEQ ID NO 12
<211> LENGTH: 25
<212> TYPE: DNA
<213> ORGANISM: Artificial sequence
<220> FEATURE:
<223> OTHER INFORMATION: probe sequence of the 31805_at probe set of
      Affymetrix, the position of said probe in the mRNA sequence of the
      fgfr3 gene being 3546

<400> SEQUENCE: 12
gcaatgcttc tagagtttta tagcc                                          25

<210> SEQ ID NO 13
<211> LENGTH: 25
<212> TYPE: DNA
<213> ORGANISM: Artificial sequence
<220> FEATURE:
<223> OTHER INFORMATION: probe sequence of the 31805_at probe set of
```

-continued

Affymetrix, the position of said probe in the mRNA sequence of the
fgfr3 gene being 3576

<400> SEQUENCE: 13
tgctaccttt caaagcttgg aggga                                           25

<210> SEQ ID NO 14
<211> LENGTH: 25
<212> TYPE: DNA
<213> ORGANISM: Artificial sequence
<220> FEATURE:
<223> OTHER INFORMATION: probe sequence of the 31805_at probe set of
      Affymetrix, the position of said probe in the mRNA sequence of the
      fgfr3 gene being 3588

<400> SEQUENCE: 14
aagcttggag ggaagccgtg aattc                                           25

<210> SEQ ID NO 15
<211> LENGTH: 25
<212> TYPE: DNA
<213> ORGANISM: Artificial sequence
<220> FEATURE:
<223> OTHER INFORMATION: probe sequence of the 31805_at probe set of
      Affymetrix, the position of said probe in the mRNA sequence of the
      fgfr3 gene being 3606

<400> SEQUENCE: 15
tgaattcagt tggttcgttc tgtac                                           25

<210> SEQ ID NO 16
<211> LENGTH: 25
<212> TYPE: DNA
<213> ORGANISM: Artificial sequence
<220> FEATURE:
<223> OTHER INFORMATION: probe sequence of the 31805_at probe set of
      Affymetrix, the position of said probe in the mRNA sequence of the
      fgfr3 gene being 3618

<400> SEQUENCE: 16
gttcgttctg tactgttact gggcc                                           25

<210> SEQ ID NO 17
<211> LENGTH: 25
<212> TYPE: DNA
<213> ORGANISM: Artificial sequence
<220> FEATURE:
<223> OTHER INFORMATION: probe sequence of the 31805_at probe set of
      Affymetrix, the position of said probe in the mRNA sequence of the
      fgfr3 gene being 3648

<400> SEQUENCE: 17
tctgggcagc tgtcccttgc ttgcc                                           25

<210> SEQ ID NO 18
<211> LENGTH: 25
<212> TYPE: DNA
<213> ORGANISM: Artificial sequence
<220> FEATURE:
<223> OTHER INFORMATION: probe sequence of the 31805_at probe set of
      Affymetrix, the position of said probe in the mRNA sequence of the
      fgfr3 gene being 3720

<400> SEQUENCE: 18
gtggccagag gtgtcaccca aaccg                                           25

The invention claimed is:

1. An in vitro diagnostic method for use with an individual having or suspected of having bladder transitional cell carcinoma (TCC), said diagnostic method being used to detect the presence of bladder TCC in said individual, to determine the stage or severity of bladder TCC in said individual, or to monitor the effect of the therapy administered to said individual, said diagnostic method comprising:
  a) detecting and quantifying an amount of fibroblast growth factor receptor 3 (FGFR3) protein in a sample of the individual, wherein the sample is a bladder tissue or urine, and
  b) comparing the amount of FGFR3 protein detected in said sample of the individual, with a first reference value from a subject without bladder transitional cell carcinoma, and
  c) comparing the detected amount of FGFR3 protein with a second reference value from a subject with advanced T2 bladder transitional cell carcinoma; wherein:
    increased levels of FGFR3 protein, relative to said first reference value, are indicative of bladder TCC, and
    increased levels of FGFR3 protein, relative to said second reference value, are indicative of bladder TCC at a stage which is less advanced than T2 bladder TCC.

2. The method according to claim 1 in which the sample is a sample of bladder tissue obtained by cystoscopy.

3. The method according to claim 1 in which the sample to be analysed is obtained from an individual not previously diagnosed with bladder transitional cell carcinoma.

4. The method according to claim 1 in which the sample to be analysed is obtained from an individual who has been previously diagnosed with bladder transitional cell carcinoma.

5. The method according to claim 1 in which the sample to be analysed is obtained from an individual receiving treatment, or who has been treated previously against bladder transitional cell carcinoma.

6. The method according to claim 1 characterised in that it comprises the extraction of the sample to obtain an extract of proteins.

7. The method according to claim 1 characterised in that the detecting and quantifying of the FGFR3 protein comprises a first step, in which the protein extract of the sample is placed in contact with a composition of one or more specific antibodies, against one or more epitopes of the FGFR3 protein, and a second step, in which the complexes formed by the antibodies and the FGFR3 protein are quantified.

8. The method according to claim 1, further comprising:
  d) comparing the detected amount of FGFR3 protein to a third reference value from a subject with Ta or T1 bladder transitional cell carcinoma, wherein:
    i) increased levels of FGFR3 protein, relative to said second reference value, are indicative of Ta or T1 bladder TCC; and
    ii) levels of FGFR3 protein which are greater than said first reference value and less than said third reference value are indicative of advanced T2 bladder TCC.

9. The method according to claim 7, characterised in that said antibodies correspond to monoclonal or polyclonal antibodies, intact or recombinant fragments of antibodies, combibodies and Fab or scFv antibody fragments, specific against the FGFR3 protein; these antibodies being human, humanised or of non-human origin.

10. The method according to claim 7 characterised in that in the detection and/or quantification of the complexes formed by antibodies and the FGFR3 protein, the techniques used are selected from the group consisting of: western-blot, ELISA (Enzyme-Linked Immunosorbent assay), RIA (Radioimmunoassay), Competitive EIA (Competitive Enzyme Immunoassay), DAS-ELISA (Double Antibody Sandwich-ELISA), immunocytochemical or immunohistochemical techniques, techniques based on the use of biochips or protein microarrays that include specific antibodies, assays based on the precipitation of colloidal gold in formats such as dipsticks; or by affinity chromatography techniques, ligand binding assays or lectin binding assays.

11. An in vitro method to assess the stage or severity of bladder transitional cell carcinoma (TCC) in an individual, that comprises:
  a) forming complexes between an antibody and a fibroblast growth factor receptor 3 (FGFR3) protein obtained from a sample of the individual, wherein the sample is a bladder tissue or urine,
  b) detecting an amount of FGFR3 protein in said sample of the individual by quantifying said complexes,
  c) comparing the amount of FGFR3 protein detected in said sample of the individual, with a first reference value from a subject without bladder transitional cell carcinoma, and
  d) comparing the detected amount of FGFR3 protein with a second reference value from a subject with advanced T2 bladder transitional cell carcinoma; wherein:
    increased levels of FGFR3 protein, relative to said first reference value, are indicative of bladder TCC, and
    increased levels of FGFR3 protein, relative to said second reference value, are indicative of Ta or T1 bladder TCC.

12. A diagnostic method for use with an individual having or suspected of having bladder transitional cell carcinoma (TCC), wherein said diagnostic method detects the presence of bladder TCC in said individual, determines the stage or severity of bladder TCC in said individual, or monitors the effect of the therapy administered to said individual, said diagnostic method comprising:
  detecting and quantifying an amount of fibroblast growth factor receptor 3 (FGFR3) protein in a sample of the individual, wherein the sample is a bladder tissue or urine, and
  comparing the amount of FGFR3 protein detected in said sample of the individual, with a first reference value from a subject without bladder transitional cell carcinoma, and comparing the detected amount of FGFR3 protein to a second reference value from a subject with Ta or T1 bladder transitional cell carcinoma,
  wherein levels of FGFR3 protein which are greater than said first reference value and less than said second reference value are indicative of advanced T2 bladder TCC.

13. The method according to claim 12 in which the sample is a sample of bladder tissue obtained by cystoscopy.

14. The method according to claim 12 in which the sample to be analysed is obtained from an individual not previously diagnosed with bladder transitional cell carcinoma.

15. The method according to claim 12 in which the sample to be analysed is obtained from an individual who has been previously diagnosed with bladder transitional cell carcinoma.

16. The method according to claim 12 in which the sample to be analysed is obtained from an individual receiving treatment, or who has been treated previously against bladder transitional cell carcinoma.

17. The method according to claim 12 characterised in that it comprises the extraction of the sample to obtain an extract of proteins.

18. The method according to claim 12 characterised in that the detecting and quantifying of the FGFR3 protein comprises a first step, in which the protein extract of the sample is placed in contact with a composition of one or more specific antibodies, against one or more epitopes of the FGFR3 protein, and a second step, in which the complexes formed by the antibodies and the FGFR3 protein are quantified.

19. The method according to claim 18, characterised in that said antibodies correspond to monoclonal or polyclonal antibodies, intact or recombinant fragments of antibodies, combibodies and Fab or scFv antibody fragments, specific against the FGFR3 protein; these antibodies being human, humanised or of non-human origin.

20. The method according to claim 18 characterised in that in the quantifying of the complexes formed by antibodies and the FGFR3 protein, the techniques used are selected from the group consisting of: western-blot, ELISA (Enzyme-Linked Immunosorbent assay), RIA (Radioimmunoassay), Competitive EIA (Competitive Enzyme Immunoassay), DAS-ELISA (Double Antibody Sandwich-ELISA), immunocytochemical or immunohistochemical techniques, techniques based on the use of biochips or protein microarrays that include specific antibodies, assays based on the precipitation of colloidal gold in formats such as dipsticks; or by affinity chromatography techniques, ligand binding assays or lectin binding assays.

* * * * *